United States Patent
Verschoor et al.

(10) Patent No.: US 7,851,166 B2
(45) Date of Patent: Dec. 14, 2010

(54) METHOD FOR DETECTING MYCOBACTERIAL INFECTION

(75) Inventors: Jan Adrianus Verschoor, Pretoria (ZA); Dismore Gilbert Ramathudi Siko, Pretoria (ZA); Sandra Van Wyngaardt, Pretoria (ZA)

(73) Assignee: The University of Pretoria, Pretoria (ZA)

( * ) Notice: Subject to any disclaimer, the term of this patent is extended or adjusted under 35 U.S.C. 154(b) by 448 days.

(21) Appl. No.: 11/579,972

(22) PCT Filed: May 11, 2005

(86) PCT No.: PCT/IB2005/051548
§ 371 (c)(1),
(2), (4) Date: Aug. 6, 2007

(87) PCT Pub. No.: WO2005/116654
PCT Pub. Date: Dec. 8, 2005

(65) Prior Publication Data
US 2009/0111125 A1    Apr. 30, 2009

(30) Foreign Application Priority Data
May 13, 2004  (ZA) ................................ 2004/3678

(51) Int. Cl.
*G01N 33/53* (2006.01)
*G01N 33/554* (2006.01)
*A61K 39/04* (2006.01)

(52) U.S. Cl. .................. 435/7.2; 424/130.1; 424/137.1; 424/163.1; 424/164.1; 424/168.1; 424/184.1; 424/234.1; 424/248.1; 435/4; 435/7.1; 435/7.32

(58) Field of Classification Search .............. 424/130.1, 424/137.1, 163.1, 164.1, 168.1, 184.1, 234.1, 424/248.1; 435/4, 7.1, 7.2, 7.32
See application file for complete search history.

(56) References Cited

U.S. PATENT DOCUMENTS 5,721,109 A    2/1998   Yano et al.
6,124,105 A    9/2000   Verschoor et al.

OTHER PUBLICATIONS

Schleicher et al., "Prevalence of anti-mycolic acid antibodies in patients with pulmonary tuberculosis co-infected with HIV," *Clinical chemistry and laboratory medicine*, vol, 40, No. 9, Sep. 2002, pp. 882-887.
Pan et al., Anti-cord factor (trehalose 6,6'-dimycolate) IgG antibody in tuberculosis patients recognizes mycolic acid subclasses, *Microbiology and immunology*, vol. 43, No. 9, 1999, pp. 863-869.

*Primary Examiner*—Robert P. Swartz
(74) *Attorney, Agent, or Firm*—Robins & Pasternak LLP

(57) ABSTRACT

A method of detecting a surrogate marker for active tuberculosis involves obtaining first, second and third samples from a subject suspected of having active tuberculosis, diluting the first sample and exposing part of it to an immobilized mycolic acid antigen in a test vessel and part of it to an immobilized mycolic antigen in a control vessel. The second sample is exposed to mycolic acid antigen-containing liposomes and the third sample is exposed to liposomes not containing mycolic acid antigens. The second sample is added to the test vessel and the third to the control vessel and binding of antibodies to the mycolic acid and antigen in both the test and control vessel is detected. The degree of binding between the test and control vessels is compared and lesser binding in the test vessel is an indicator of the presence of antibodies to the mycolic acid antigen.

15 Claims, 5 Drawing Sheets

A

B

METHOD FOR DETECTING MYCOBACTERIAL INFECTION

CROSS-REFERENCE TO RELATED APPLICATIONS

This application is a §371 filing of PCT/IB2005/051548, filed May 11, 2005, which claims priority to ZA 2004/3678, filed May 13, 2004, from which applications priority is claimed pursuant to the provisions of 35 U.S.C. §119 and §120, which applications are incorporated herein by reference in their entireties.

This invention relates to a method for detecting active tuberculosis. In particular, the invention relates to a serodiagnostic method for tuberculosis based on the prevalence of antibodies in mammalian subjects to lipid antigens derived from *Mycobacterium tuberculosis*. For a disease such as tuberculosis, there has been no acceptable serodiagnostic assay up until now, despite the fact that much progress has been reported in studies of antibodies to various antigens of *M. tuberculosis* in the serum of patients with TB (Pan et al., 1999; Julian et al., 2002; Schleicher et al., 2002; Lopez-Marin et al., 2003; Pottunarthy et al., 2000).

Mycobacterial diseases are the cause of a high mortality in humans and other mammals. This is mainly due to the resilience of the pathogenic mycobacteria. These hard to eradicate bacteria have a low multiplication rate and hide intracellularly in the host macrophages. Treatment for mycobacterial diseases comprises combination chemotherapy extending over many months. This increases the frequency of non-compliance and thus may contribute to the emergence of multi-drug resistant strains of mycobacteria (Heym, Honore et al., 1994).

The current problems in the diagnosis and treatment of mycobacterial diseases can be considered using tuberculosis as an example. Tuberculosis (TB) is a chronic pulmonary or extra-pulmonary disease caused by infection with *Mycobacterium tuberculosis* (*M. tuberculosis*). *M. tuberculosis* is spread primarily through aerosolized infectious particles generated from coughing and sneezing by individuals with pulmonary TB (Fenton and Vermeulen, 1996). After being inhaled, the bacilli are able to reach the terminal pulmonary airways and alveoli of uninfected individuals (Lawn et al., 2002). Tuberculosis remains a major global health problem despite advances in medical science and a range of effective drugs, which for some time created the impression that the disease had been conquered. One third of the world's population is estimated to be infected with *M. tuberculosis*. It is further estimated that more than 8 million people contract TB every year, resulting in over 2 million deaths. The global tuberculosis incidence is 61 new cases per 100,000 people (Johnson, 2000).

The World Health Organization in 1993 declared TB a global emergency (WHO, 1993). The incidence of TB in developing countries has always been high, but even industrialized countries are currently experiencing the re-emergence of the disease mainly resulting from the global HIV epidemic and increased migration. Although about 10% of *M. tuberculosis* infected people are expected to develop tuberculosis during their lifetime, the situation is aggravated by co-infection with HIV as this increases the risk of developing TB by a factor of 30. It is estimated that TB is responsible for 32% of deaths among HIV-positive people globally, compared to 11% due to septicaemia, 10% to cerebral toxoplasmosis, 8% to pneumonia, 6% to malignancies, 5% to meningitis and 10% due to other infections (Narain et al., 1992). Approximately 8% of the TB patients and one quarter of those who died of TB were already co-infected with HIV, and it is likely that this proportion will increase in future (Kaufmann and Hess, 2000).

The re-emergence of TB as a global health threat can be attributed to the following:
1. Insufficient protection of adults by the world-wide BCG vaccination programme
2. Problems associated with TB diagnosis
3. Problems associated with compliance to the lengthy TB treatment and the occurrence of *M. tuberculosis* multi-drug resistant strains
4. Tuberculosis co-infection with HIV infection
5. Socio-economic aspects Tuberculosis Detection The basis for effective treatment and cure of patients is the rapid diagnosis of the disease and its causative agent, which is based on assessment of clinical symptoms combined with laboratory tests (Reischl, 1996). Basically, there are five different possibilities for laboratory diagnosis of tuberculosis:
1. Measurement of hypersensitivity to mycobacterial antigens (e.g. tuberculin skin test)
2. Direct detection of the pathogens (e.g. microscopy and/or culture)
3. Detection of protein components of the pathogens with the help of specific antibodies
4. Specific detection of antibodies directed against the pathogen and changes in their corresponding titer
5. Specific detection of nucleic acids of the pathogen (which usually requires culture of the pathogen after sampling)

Several studies have demonstrated that the skin test cannot reliably distinguish between previous *Mycobacterium bovis* BCG vaccination, exposure to environmental mycobacteria, or infection with *M. tuberculosis* (Charnace and Delacourt, 2001; Chan et al., 2000). It is also known to give false negative results in patients co-infected with HIV. Traditional microscopy detection methods (acid fast bacilli sputum smear test) have major disadvantages of not being sensitive enough, not being able to distinguish between live and dead bacilli or between pathogenic and non-pathogenic species of mycobacteria and of being poorly predictive in HIV co-infected patients (Palmieri et al., 2002). Although culture of bacteria is the reference standard In diagnosis and follow-up of disease, it can take up to 6-8 weeks to grow and identify *M. tuberculosis* (Raqib et al., 2003) and HIV sero-positive patients with normal chest X ray and sputum smear negative assay may be missed (Palmieri et al., 2002). Tests based on antibody detection suffer from a high rate of false positives due to the BCG vaccination that most people are subject to, or false negatives due to immune compromise, such as with co-infection with the immune paralyzing HIV virus that hinders antibody formation (Boggian et al., 1996). The use of molecular approaches to the diagnosis of TB has provided rapid and sensitive detection tools, but these approaches are expensive and require specially trained personnel (Kivihya-Ndugga et al., 2004). For these reasons they are not suitable for detecting TB in resource-poor, TB-endemic regions, already overburdened with the cost of controlling the disease (O'Brien, 1995, Voelker, 1995).

According to a first aspect of the invention, there is provided a method of detecting a surrogate marker for active tuberculosis, the method including the steps of
taking up isolated mycolic acid antigen of mycobacterial origin or a synthetic analogue thereof in a liposome carrier to produce mycolic acid antigen-containing liposomes;

immobilizing isolated mycolic acid antigen of mycobacterial origin to produce immobilised antigens;

obtaining a first, a second and a third sample from a human or animal suspected of having active tuberculosis, wherein each sample may contain antibodies to the antigen, the first sample having a lower concentration by dilution than the second and third samples;

exposing part of the first sample to the immobilised mycolic acid antigen in a test vessel;

exposing part of the first sample to the immobilised mycolic acid antigen in a control vessel;

exposing the second sample to mycolic acid antigen-containing liposomes;

exposing the third sample to liposomes not containing the mycolic acid antigen;

adding the second sample, after exposure to the mycolic acid antigen-containing liposomes, to the test vessel;

adding the third sample, after exposure to the liposomes not containing the mycolic acid antigen, to the control vessel;

detecting binding of antibodies to the mycolic acid antigen in both the test and control vessels in real time; and comparing the degree or extent of binding between the test and the control vessels, any observed lesser binding in the test vessel being an indicator of the presence of antibodies to the mycolic acid antigen in the samples that relates to active tuberculosis in the human or animal from which the samples originated.

The mycobacterial infection may be of the type which causes diseases selected from pulmonary and extra-pulmonary tuberculosis.

The mycolic acid antigen may be derived from mycobacteria selected from virulent and pathogenic mycobacteria. In particular, the mycolic acid antigen may be derived from *Mycobacterium tuberculosis*.

The mycolic acid antigen may be in a form selected from homogenous and heterogenous compound mixtures. In a preferred embodiment of the invention the mycolic acid antigen is first mixed with a phospholipid such as phosphatidylcholine to produce liposomes having mycolic acid antigen integrated into the liposome phospholipid surface layer. Typically, production of liposomes will involve sonication of the phospholipid-antigen mixture.

The mycolic acid antigen-containing liposomes in the test and control vessels to which the first sample is exposed may be immobilized mycolic acid antigen. Methods of immobilization may include methods known to one skilled in the art. Preferably the mycolic acid antigen-containing liposomes may be immobilized on an activated surface. In a preferred embodiment of the invention the activated surface may be a hydrophilic, underivatised biosensor cuvette surface which has been activated by prior incubation with a surface binding agent linked to a hydrophobic hydrocarbon and then washed with a suitable buffer. The agent may be a cationic detergent, such as cetyl-pyridine chloride (CPC).

In the method of the invention, the antibody to the mycolic acid antigen serves as a surrogate marker for active tuberculosis.

The samples from a human or animal suspected of having active tuberculosis may be selected from blood samples, spinal fluid samples and samples that naturally contain antibodies. In the case of a human or animal with active mycobacterial disease the sample will contain antibodies to the mycobacterial pathogen.

The sample may be from an HIV positive human.

The antibodies may be antibodies against *Mycobacterium tuberculosis*, or antibodies against part thereof. The antibodies may be of the type that demonstrate cross-reactivity towards sterols such as cholesterol. The antibodies may be low affinity antibodies.

The samples from a human or animal suspected of having active tuberculosis may be further prepared such that any antibodies present in the sample are enriched, precipitated or partially purified, and present in non-complexed form. Such methods of preparation are known to one skilled in the art.

The first, second and third samples from a human or animal suspected of having active tuberculosis will preferably be derived from an original sample by dividing the original sample into at least the first, second and third samples before dilution.

Exposure of the second sample of human or animal origin to mycolic acid antigen may include pre-incubation of the second sample with liposomes containing mycolic acid antigen. Typically the control for this pre-incubation will include pre-incubation of the third sample with empty liposomes, or liposomes containing phospholipid only.

Exposure of the first sample of human or animal origin to mycolic acid antigen in the test and control vessels may include exposing the samples of human or animal origin to a surface prepared by the prior coating of the surface with mycolic acid antigen and a suitable blocking reagent. Typically such a blocking reagent is saponin or casein.

The detection of binding of antibodies and/or other material to the mycolic acid antigen may be carried out in an automated device. Preferably the method will be carried out in a resonant mirror or surface plasmon resonance biosensor, or a sensor based on the monitoring of piezo-electrical signals.

The detection of the binding of the antibodies and/or other material to the mycolic acid antigen may be carried out in real time.

The Applicants have found that simply measuring the extent of binding of antibodies to mycolic acids in a sample of human or animal origin to an immobilized mycobacterial antigen is not a reliable diagnostic method for detecting antibodies to the immobilized antigen because of interfering or competing interactions with other components in the sample. The Applicant's finding that prior exposure of a part of the sample to free antigen to selectively reduce the amount of free antibodies to the antigen before detecting antibody binding to mycolic acid in the test vessel is a key aspect of the invention. This reduction is detected in the comparison of the degree or extent of binding in the test and control vessels and is a clear indication of the presence of antibodies to the antigen in the original sample.

The Applicants have also found that simply measuring the extent of binding of antibodies to mycolic acids in a sample of human or animal origin to an immobilized mycobacterial antigen, after washing away excess of unbound antibody, is not a reliable method for detecting antibodies to an immobilized antigen because of the low affinity of the antibodies to mycolic acids in most individuals.

Further features of the invention will now become apparent in the following description with reference to the following non-limiting examples and with reference to the accompanying figures in which.

Figure 3:
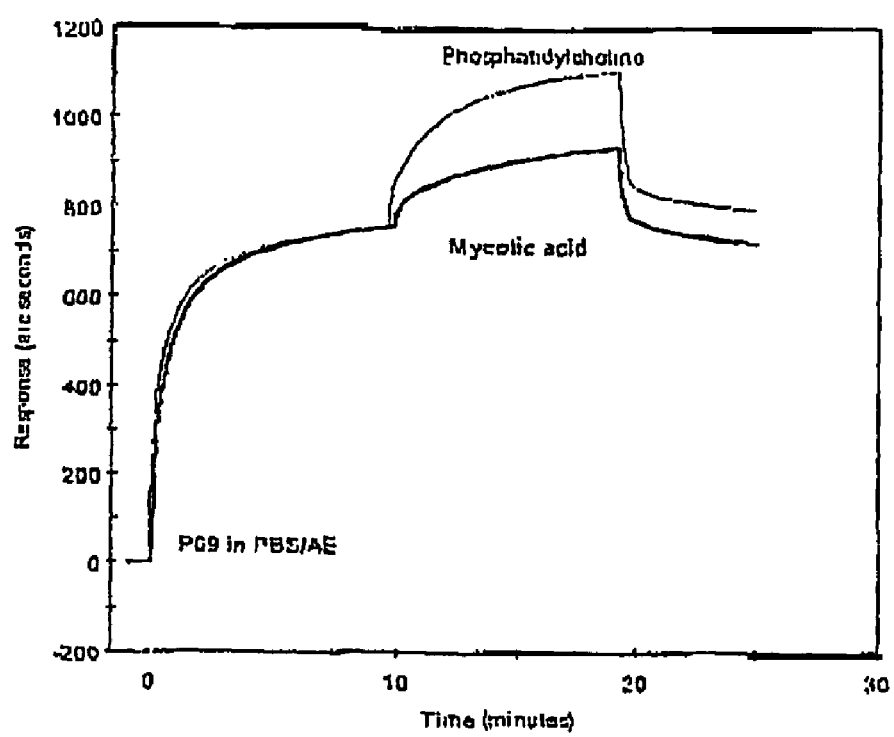
Figure 3:
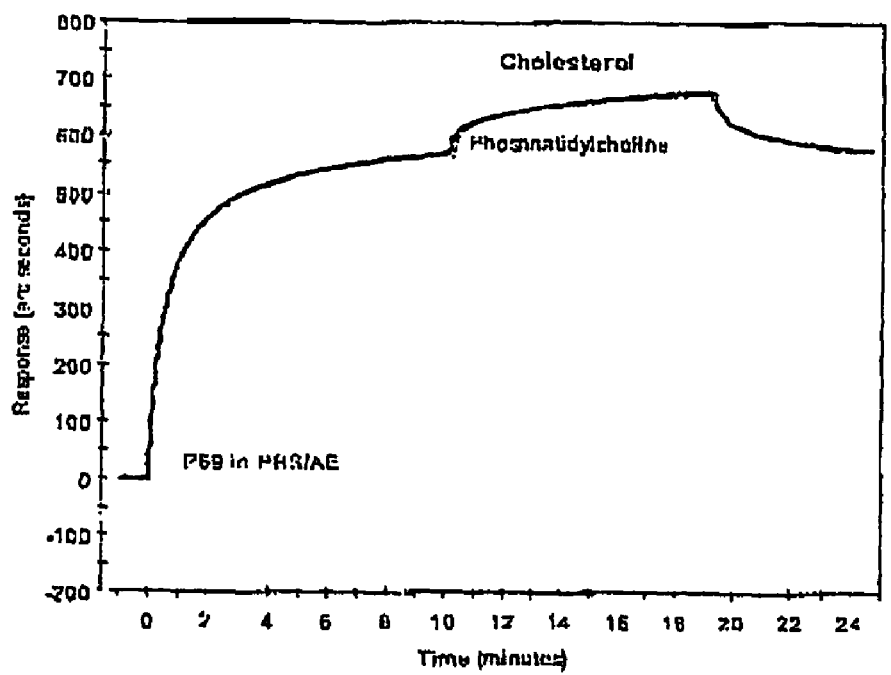
Figure 4:
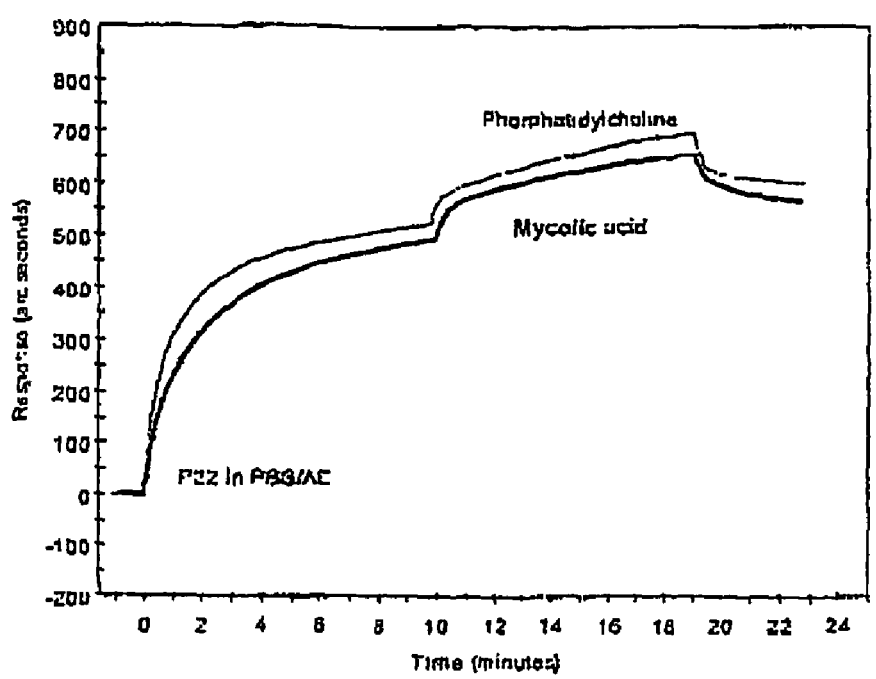
Figure 4:
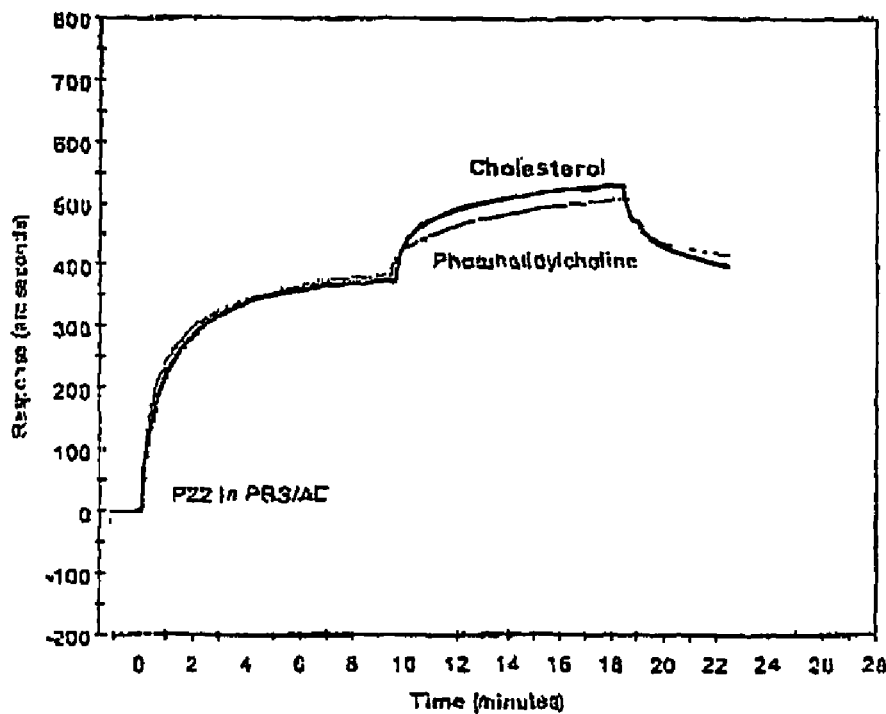
Figure 5:
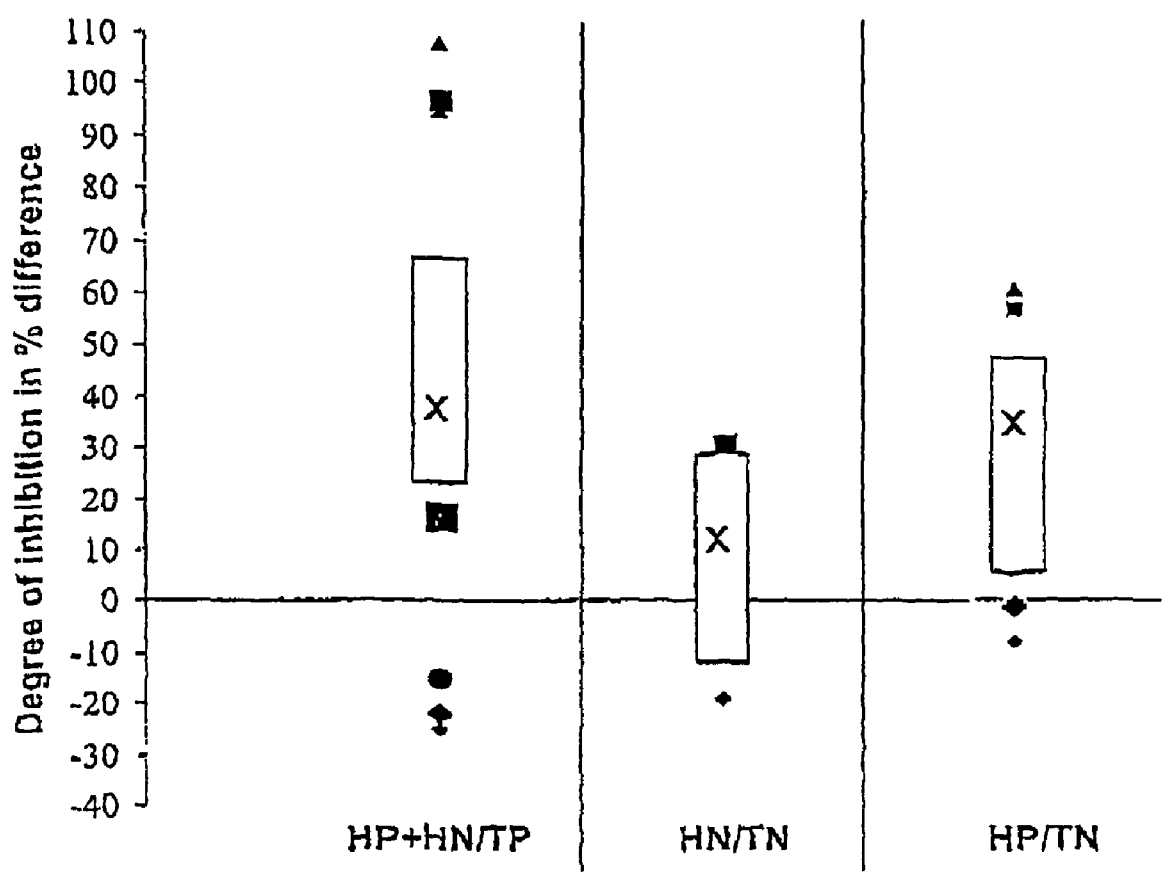

FIG. 3 shows the inhibition of human TB+ patient (HIV+) serum antibody binding on a mycolic acids immobilized surface of the IAsys cuvette, FIG. 4 shows the inhibition of human TB− patient serum antibody binding on a mycolic acids immobilized surface of the IAsys cuvette; and FIG. 5 shows the percentage of inhibition of binding of biosensor signal in TB+ patients and TB− controls after pre-incubation of sera with mycolic acids and phosphatidylcholine liposomes before testing on mycolic acids coated cuvettes. HP+HN/TP denotes the TB positive population (n=31) that contained HIV positive as well as HIV negative patients. HN/TN denotes the TB negative population which were also HIV negative (n=11), while HP/TN denotes the TB negative population which were HIV positive (n=18). Solid symbols represent the individual biosensor readings of different samples analyzed. Rectangles indicate where 75% of the data in each group clusters. The crosses inside the rectangles give the median values for each group.

Figure 1:
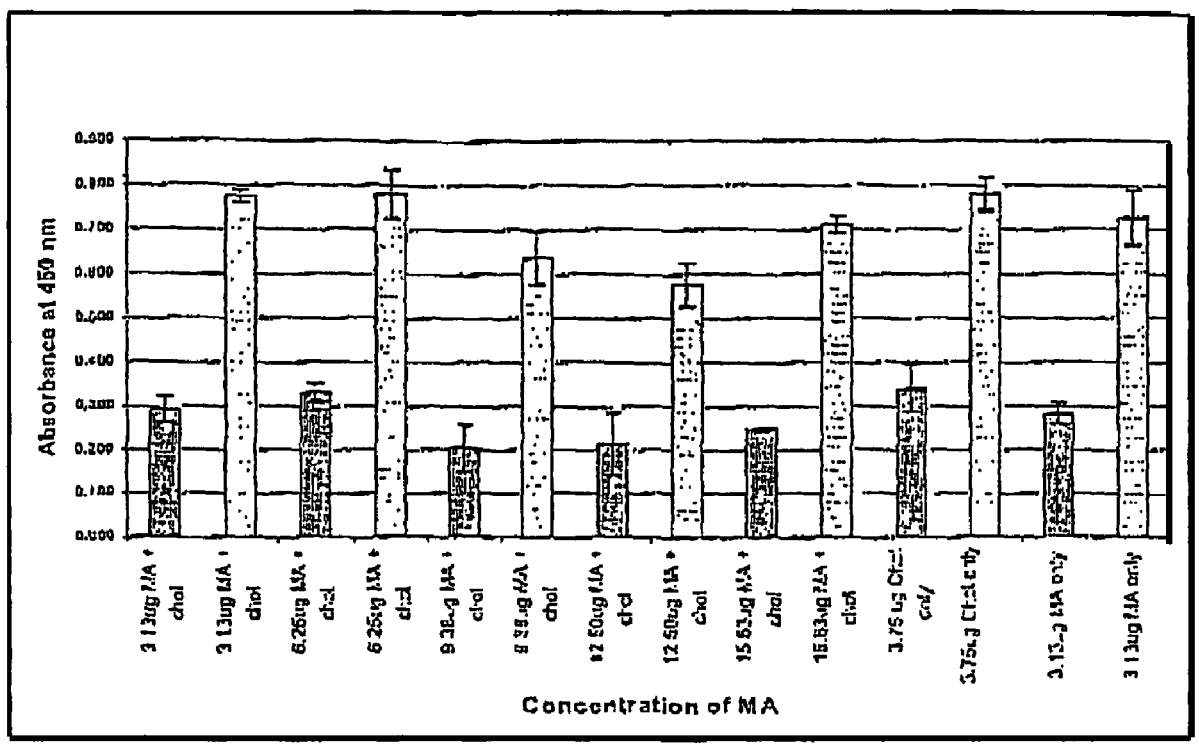
FIG. 1 shows an ELISA comparison of patient and healthy control sera on natural mycolic acid and cholesterol coated wells.
Figure 2:
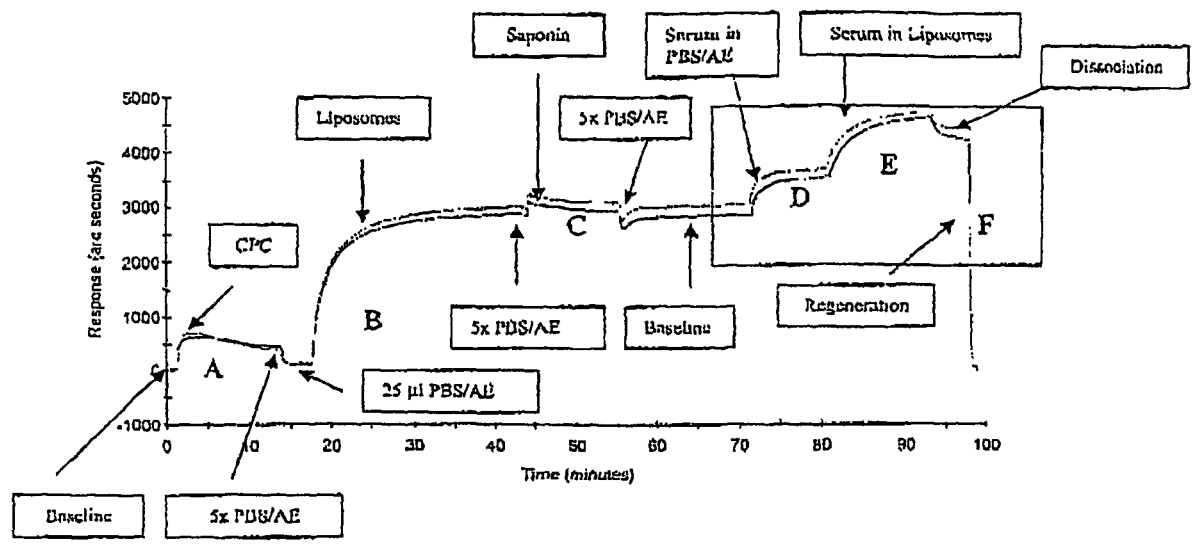
FIG. 2 shows a typical graph that summarizes the process of measuring antibody binding or inhibition of binding by cholesterol or mycolic acid and phosphatidylcholine liposomes, on an IAsys biosensor cuvette surface coated with mycolic acid or liposomes.

In FIG. 1 the comparison is of patient and healthy control sera on mycolic acid and cholesterol-coated wells containing a concentration range of mycolic acid with the addition of 3.75 µg of cholesterol per well as antigen. All sera were tested in a 1:60 dilution. The negative control has sample identity: DR and the positive control has sample identity: Patient 1799 from 1994. In FIG. 2 the surface was activated with CPC and (A), coated with mycolic acids of cholesterol liposomes (E), blocked with saponin (C), calibrated with a high dilution of serum (D), applied to measure the binding and disassociation of inhibited sera at lesser dilution (E), and regenerated with KOH and ethanol (F), In FIG. 3, for the first 10 minutes, a 1:1000 dilution of serum (sample identity P69) in PBS/AE was incubated in both cells. For inhibition studies, the pre-incubated serum in a dilution of 1:500 was then added. (A) Inhibition with mycolic acids or phosphatidylcholine and (B) inhibition with cholesterol or phosphatidylcholine. In FIG. 4, for the first 10 minutes, a 1:1000 dilution of serum (sample identity P22) in PB/AE was incubated n both cells. For inhibition studies, the pre-incubated serum in a dilution of 1:500 was then added. (A) Inhibition with mycolic acids or phosphatidylcholine and (B) inhibition with cholesterol or phosphatidylcholine. In FIG. 5 HP+HN/TP denotes the TB sensitive population (n=31) that contained HIV positive as well as HIV negative patients. HN/TN denotes the TB negative population which were also HIV negative (n=11), while HP/TN denotes the TB population which were HIV positive (n=18). Rectangles indicated where 75% of the data in each group cluster. The crosses inside the rectangles give the median values for each group.

DESCRIPTION OF THE INVENTION

Mycolic acids (MA) are high molecular weight, α-alkyl, β-hydroxyl fatty acids and are characteristic components of the cell envelope of mycobacteria and some other bacterial general. In the mycobacterial cell envelope, MA are present as free lipids, such as trehalose dimycolate (TDM) or cord factor and trehalose monomycolate (TMM), but for the most part, they are esterified to the terminal penta-arabinofuranosyl units of arabinogalactan, a peptidoglycan-linked polysaccaride (Brennan and Nikaido, 1995). The presence of such long-chain fatty acids is largely responsible for the high hydrophobicity and very low permeability of the mycobacterial cell envelope (Lee et al., 1996). The number of carbon atoms that make up the MA varies from $C_{20}$ to $C_{30}$ in the genus Corynebacterium to $C_{80}$ to $C_{90}$ in the genus Mycobacterium. MA of the Nocardia and Rhodococcus species have lengths ranging from $C_{36}$ to $C_{66}$ (Butler et al., 1991). Mycobacterial MA compose about 40-60% of the dry weight of the cell wall of the bacteria (Brennan and Nikaido, 1995; Lee et al., 1996). Because of the uniqueness of the structures of mycolic acids to the pathogenic Mycobacterium tuberculosis, they would provide ideal antigens for serodiagnosis of tuberculosis.

PCT Patent Application No. PCT/GB95/00856 (Verschoor and Bye, 1995) relates to the incorporation of mycolic acid in an immunogenic conjugate which elicited specific antibody production in mice. Optimization of a procedure for extraction and purification of mycolic acids of mycobacteria was disclosed in PCT Patent Application No. PCT/GB96/00416 (Verschoor, 1996 and Goodrum et al., 2001). The immunological properties of the mycolic acids were tested in TB infected animals and in vitro cultures of human cells to explore the potential for broader application of the patented principles and products of tuberculosis. This work has been compiled in PCT Patent Application No. PCT/GB98/00681 (Verschoor et al., 1998) and published (Korf et al., 2005). In the USA, four divisional patent applications were made from this, of which divisional PA129709/US was conditionally allowed in the USA in 2002, relating to the use of anti-mycolic acid antibodies in human subjects as surrogate markers for TB infection. The claim could not, however, be substantiated with experimental data, as it was not yet known at the time how to demonstrate the prevalence of anti-mycolic acid antibodies with adequate accuracy in serum samples of human or animal origin.

Pan et al., (1999) indicated that the anti-mycolic acid antibodies (IgG) in TB patients specifically recognized mycolic acid structure, especially methoxy mycolic acid. Mycolic acid Is presented by antigen-presenting cells (APC) through a mechanism that does not involve MHC-class I or MHC-class II molecules. Mycolic acid is a CD1 restricted antigen with the ability to induce proliferation of a T-cell line (Beckman et al., 1994). The human CD1 protein is known to mediate T-cell responses by presenting at least the three classes of mycobacterial lipids, i.e. free mycolates, glycosylated mycolates and diacylglycerol based glyco-phospholipids, such as lipoarabinomannan (Beckman et al., 1994; Moody et al., 1997). The alkyl chains of the mycolic acid antigen have been proposed to bind directly within the hydrophobic groove of CD1 resulting in presentation of the hydrophilic caps to the T-cell's antigen receptor (Moody et al., 1999; Porcelli et al., 1996). The CD1-restricted lipid antigen presentation pathway could probably be the reason why the antibody response to mycolic acids is preserved in HIV-seropositive patients despite a declining CD4 T-lymphocyte count as the T cells that are stimulated by the mycolic acid presentation need not express the CD4 surface protein (Schleicher et al., 2002).

EXAMPLE 1

ELISA Assays for Detection of Antibodies in Serum from Tuberculosis Patients 1.1 Materials 1.1.1 Mycolic Acids Mycobacterial mycolic acids were isolated from a culture of Mycobacterium tuberculosis H37Rv (American Type Culture Collection 27294) as described by Goodrum et al., (Goodrum et al., 2001).

1.1.2 ELISA Reagents

PBS buffer: 8.0 g NaCl, 0.2 g KCl, 0.2 g $KH_2PO_4$ (anhydrous) and 1.05 g $Na_2HPO_4$ (anhydrous) per 1 l distilled water, adjusted to pH 7.4.

Diluting buffer: 0.5% (m/v) carbohydrate- and fatty acid free casein (Calbiochem, La Jolla, Calif.) in PBS buffer adjusted to pH 7.4 was used for diluting of the sera and the immunoreagents.

Blocking buffer: same as diluting buffer and used for blocking of ELISA plates.

Washing buffer: same as diluting buffer and used for washing of ELISA plates.

Coating antigens: Mycolic acids originating from *Mycobacterium tuberculosis*, isolated as described above, and cholesterol (Sigma, St. Louis, Mo.; Cat No C-8667) were used at final concentrations of 60 µg/ml and 75 µg/ml, respectively. To prepare the coating solutions, the antigens were heated in PBS buffer for 20 min at 85° C. The hot solutions were sonicated at 20% duty cycle and optimal output level for 1 min. The solutions were kept at 85° C. and loaded into the ELISA plates.

Conjugates: Goat anti-human IgG (H+L chains) antibody conjugated to peroxidase was obtained from Sigma (Cat No A-8667).

Substrate: o-Phenylenediamine (Sigma; Cat No P-1526) and hydrogen peroxide (Merck, Darmstadt, BRD; Cat No BDR 10366).

Substrate buffer: 0.1 M citrate buffer (0.1 M citric acid and 0.1 M tri-sodium citrate, adjusted to pH 4.5).

1.1.3 Human Sera

Human sera were negative control sera from people who had never suffered from tuberculosis and sera obtained from a patient who had been diagnosed with tuberculosis.

1.1.4 Plasticware

The following plasticware was used:

ELISA plates: flat-bottom 96-well plates (Serowell; Bibby Sterilin Ltd, Stone, UK)

Sterile, disposable 50 ml centrifuge tubes (Bibby Sterilin)

Disposable pipettes (Bibby Sterilin)

Disposable pipette tips (Bibby Sterilin)

1.2 Methods

1.2.1 Antigen Coating of ELISA Plates

The respective antigens were dissolved in hot PBS and then sonicated, as described above. The wells of flat-bottom ELISA plates were coated overnight at 4° C. with 50 µl/well of antigen solution. The final antigen load was maximally 3.1 µg/well for mycolic acids and 3.75 µg/well for the cholesterol.

1.2.2 Blocking of ELISA Plates

The coating solution was flicked out of the plates and replaced with 400 µl blocking buffer per well. Blocking was carried out for 2 hours at room temperature.

1.2.3 Binding of Human Antibodies

The blocking solution was aspirated from the wells before loading of the serum or serum precipitate samples. Sera were diluted 20 times in diluting buffer. Aliquots of 50 µl were introduced into wells in quadruplicate. The plates were incubated at room temperature for 1 hour. The serum samples were removed from the wells, the wells washed three times with washing buffer using an Anthos Autowash automatic ELISA plate washer and then emptied by aspiration.

1.2.4 Detection of the Bound Antibodies

Peroxidase-conjugated anti-human IgG diluted 1:1000 in diluting buffer was introduced in aliquots of 50 µl per well and the plates were incubated for 30 min at room temperature. After removal of the conjugate, the wells were washed three times with the washing buffer and then emptied by aspiration.

The substrate solution comprising 10.0 mg o-phenylenediamine and 8.0 mg hydrogen peroxide in 10 ml of 0.1 M citrate buffer pH 4.5, was prepared immediately before use and introduced in 50 µl aliquots per well. The plates were incubated at room temperature and the colour development was monitored at 5, 30 and 60 min after addition of the substrate using an SLT 340 ATC photometer at a wavelength of 450 nm.

1.3 Results and Discussion

Patients who have active (smear and culture positive) pulmonary TB have elevated levels of specific antibodies to *M. tuberculosis* mycolic acids compared to humans without evidence of TB. These antibodies were detected by an enzyme-linked immunosorbent assay (ELISA). The results, presented in FIG. 1, showed that TB patient sera could be distinguished from a negative control serum by displaying higher antibody binding on mycolic acids-coated plates. The positive TB serum (sample identity: Patient 1799) was the strongest anti-MA antibody binding signal producing serum selected from more than 200 TB patient serum samples. The results also indicated the cross-reactivity of antibody binding to mycolic acids and cholesterol. Almost identical signals were produced in wells coated either with cholesterol, or mycolic acids alone. It was also indicated that mixtures of mycolic acids and cholesterol in the coat did not affect the signal to any significant degree. This result suggests a cross-reactivity of binding of TB patient antibodies between mycolic acid and cholesterol and supported the hypothesis of a molecular mimicry between mycobacterial mycolic acids and cholesterol (Siko, 2002).

Anti-cholesterol antibodies are commonly found in human sera and may be induced by a variety of diseases (Horvath and Biro, 2003, Horvath et al., 2001, Alving and Wassef, 1999, Dijkstra et al., 1996). This could be problematic for a serodiagnostic assay that is based on the prevalence of anti-mycolic acids antibodies and may be the cause of the many false positive sera that were registered with the ELISA technique to determine such antibodies in hospitalized $TB^+$ and $TB^-$ patients (Schleicher et al., 2002). The specificity of binding of antibodies to cholesterol and mycolic acids was then confirmed on an affinity biosensor (Cush et al., 1993, Myszka, 1999)) as indicated in example 2.

EXAMPLE 2

Biosensor Assays for Recognition of Antibodies in Serum from Tuberculosis Patients

2.1 Materials

2.1.1 Resonant Mirror Biosensor Apparatus

The IAsys resonant mirror biosensor system (Buckle et al., 1993) and twin-cell non-derivatized cuvettes were from Affinity Sensors (Cambridge, United Kingdom).

2.1.2 Human Sera

Serum samples were selected from 102 patients (aged between 18 and 65) half of whom had active pulmonary tuberculosis. The study population consisted of a tuberculosis-positive ($TB^+$) group and a control tuberculosis-negative ($TB^-$) group. The $TB^+$ group consisted of patients with newly diagnosed smear-positive pulmonary tuberculosis of which approximately 50% were HIV-seropositive. The TB⁻ patients of whom approximately 50% were HIV seropositive had medical conditions other than TB and were recruited from the general medical wards. None of the TB⁺ patients were on anti-TB chemotherapy at the time of serum collection.

2.1.3 Mycolic Acids

Mycobacterial mycolic acids were isolated from a culture of *M. tuberculosis* H37Rv (American Type Culture Collection 27294) as described by Goodrum et al., (2001).

2.1.4 Biosensor Reagents

PBS/EA buffer: 8.0 g NaCl, 0.2 g KCl, 0.2 g $KH_2PO_4$ and 1.05 g $Na_2HPO_4$ per 1 l ultrapure, distilled water with 1 mM EDTA and 0.025% (m/v) sodium azide, adjusted to pH 7.4

Cetylpyridinium chloride (CPC; Sigma, St. Louis, Mo.; Cat No C-9002) 0.02 mg per ml of PBS/EA buffer Cholesterol (5-cholesten-3β-ol) (Sigma; Cat No C-8667): stock solution 100 mg per ml in chloroform (Merck, Darmstadt, BRD)

Phosphatidyl choline (pure) (PC-99; Sigma; Cat No P-3556): stock solution 100 mg per ml in chloroform HCl 0.1 M NaOH 10 mM Ethanol (Saarchem, SA) 96% (v/v) in demineralized water Saponin (Sigma; Cat No S-1252), 1 mg/ml in PBS/EA buffer 2.2 Methods 2.2.1 Preparations of Liposomes Stock solutions of cholesterol and phosphatidylcholine (100 mg/ml) were prepared by dissolving the weighed amounts in chloroform. Cholesterol containing liposomes were prepared by combining 30 µl cholesterol and 60 µl phosphatidylcholine (Sigma St Louis, Mo.) stock solutions. Mycolic acids containing liposomes were prepared by adding 90 µl phosphatidylcholine stock to 1 mg dried mycolic acids. Empty liposomes, i.e. without cholesterol and mycolic acids, were prepared by taking 90 µl of phosphatidylcholine stock solution. During pipetting, everything was kept on ice to avoid evaporation of chloroform. The liposome ingredients were dried with nitrogen gas in a heat block at 85° C. for about 10 minutes. Liposome formation was induced by addition of 2 ml saline (0.9% NaCl) and placing in a heat block at 85° C. for 20 minutes, with vortexing every 5 minutes. The liposomes were then sonicated for 2 minutes at 30% duty cycle at an output of 3% with the Model B-30 Branson sonifier (Sonifer Power Company, USA). The sonicator tip was thoroughly washed with chloroform and rinsed with distilled water before and after use. The liposomes (200 µl) were aliquoted into 10 tubes and kept at −20° C. overnight before freeze-drying. After freeze-drying, 2 ml of PBS/AE was added to each tube containing liposomes. The tubes were placed in a heat block for 20 minutes and sonicated as before.

2.2.2 Detection of Anti-Mycolic Acids in Human Sera on IAsys Affinity Biosensor

IAsys software was used to set the device at a data-sampling interval of 0.4 s, temperature of 25° C. and stirring rate of 75% for all experiments on the IAsys affinity biosensor. The cells were rinsed three times prior to use with ethanol (98%) followed by extensive washing with PBS/AE. A 60 µl volume of PBS/AE was pipetted into each cell of the cuvette to obtain a stable baseline for 1 minute. The PBS/AE was subsequently aspirated and the surface-activated with 50 µl of cetyl-pyridinium chloride (CPC) for 10 minutes. This was followed by 5 times washing with 60 µl PBS/AE and then substituting with 25 µl PBS/AE for a new baseline before immobilization of mycolic acids containing liposomes to the surface for 20 minutes. The Immobilized liposomes were then finally washed 5 times with 60 µl PBS/AE and substituted with 50 µl of saponin, incubated for 10 minutes. This latter step was to avoid non-specific binding of other molecules on the surface of the cuvette during the subsequent binding events.

The surface was then washed 5 times with PBS/AE and each cell's content was substituted with 25 µl of PBS/AE and allowed to equilibrate for about 5-10 minutes to achieve a stable baseline. Inhibition studies were performed using patient serum that was first placed at room temperature to thaw completely. After obtaining a stable baseline, a 1:1000 dilution of serum antibodies (10 µl) in PBS/AE was added, to compare the response of the two cells over 10 minutes. A pre-incubation of 1:500 dilutions of serum antibodies with liposomes containing either mycolic acids or cholesterol, or empty liposomes (phosphatidylcholine alone) were allowed for 20 minutes. These were then added (10 µl) for inhibition studies in different cells, one with mycolic acids or cholesterol liposomes and the other with phosphatidylcholine as a control, and allowed to bind for 10 minutes. Finally, dissociation of antibodies was effected with 3 times PBS/AE washing and measurement of the response for 5 minutes.

2.2.3 Regeneration of Non-Derivatized Cuvettes

Regeneration was effected by initial 3 times washing with 96% ethanol for one minute, followed by 7 times washing with 70 µl PBS/AE for 1 minute. The surface was then finally treated with 50 µl potassium hydroxide (12.5 M) for 2 minutes and followed by 7 times washing with 70 µl PBS/AE for 1 minute.

2.3 Results and Discussion

The six main stages involved to measure the binding of specific antibodies to lipid antigens in liposomes in real time are: (A) the activation of the surface with CPC, (B) immobilization of the liposomes containing cholesterol or mycolic acids to the surface, (C) blocking with saponin to prevent non-specific protein binding, (D) binding (association) of antibodies from a high dilution of serum to calibrate the signal of the two cells of the cuvette, (E) the binding and dissociation of inhibited patient sera at lesser dilution, and finally (F) surface regeneration (FIG. 2).

2.3.1 Detection of Anti-Mycolic Acids Antibodies in Human Sera

Patient sera selected from the collection of Schleicher et al., (2002) were used to detect antibodies against mycolic acids or cholesterol on the optical IAsys biosensor. The ELISA experiments were performed as described in Schleicher et al., (2002). Since it was proposed that there could be a mimicry between cholesterol and mycolic acids structures (see Example 1) it was important to test the specificity of binding to determine if the antibodies directed to mycolic acids would also bind cholesterol in the biosensor assay. This was determined by pre-incubating test serum with either mycolic acids—or cholesterol—containing liposomes and applying these on biosensor cuvettes coated with mycolic acids. In the control experiments sera were pre-incubated with empty liposomes (phosphatidylcholine only) containing neither mycolic acids, nor cholesterol. The pre-incubation of a sputum positive TB patient serum with mycolic acids liposomes resulted in an inhibition of antibody binding on a cuvette surface coated with mycolic acids when compared to the signal generated by the same serum pre-incubated with phosphatidylcholine liposomes (FIG. 3A). This confirmed the specificity of binding of antibodies to mycolic acids in sputum positive TB patient's sera. There was no apparent inhibition of antibody binding when the same patient serum was pre-incubated with cholesterol liposomes (FIG. 3B). The results suggest that the anti-mycolic acids antibodies in tuberculosis patients have a higher affinity for mycolic acids than for cholesterol No inhibition of binding was observed when a sputum negative control serum (HIV⁻TB⁻) was pre-incubated with liposomes containing either mycolic acids (FIG. 4A) or cholesterol (FIG. 4B) and tested on the biosensor to determine binding of antibodies to mycolic acids. This shows that specific anti-mycolic acids antibodies may only be demonstrated in TB⁺ patients, but not in TB⁻ controls after pre-incubation of serum with mycolic acids.

The raw data from the biosensor analyses of 102 TB patient and control sera were assessed for accuracy of measurement and interpretation and the following criteria were applied:

The cuvette cell calibration curves of the high dilution serum in the two cells of one cuvette had to fall within 90-100% Identity in terms of the relative response amplitudes.

Calibration curve profiles had to be similar by eye.

The amplitude of binding of the calibration curves had to be at least the average of all 102 samples analyzed minus one standard deviation.

This translated into 480−145=335 arc.sec as minimum response amplitude required for the calibration curve.

When sample runs were repeated, the result had to be reproducible.

Of the 102 sera that were analyzed, 61 met the criteria above. These were divided into 32 TB positive (HPTP+ HNTP), 11 HNTN=HIV negative, TB negative and 18 HPTN samples (FIG. 5).

The 18 HPTN sera were omitted in the calculation of the performance parameters of the test based on the 61 data points, as it is known that the reference standard of sputum growth of mycobacteria does not measure accurately in this population. Accuracy of the assay was then found to be 35/43=81%, sensitivity was 25/32=78%, specificity was 10/11=82%, total positive/clinical positive=26/32=81%. The average percentage inhibition for the TB+ population was 40±30 and the TB− population 11±16. When only the HPTP were compared to the HPTN patients, accuracy of the assay was found to be 25/41=61%, sensitivity was 18/23=78%, specificity was 7/18=39%, total positive/clinical positive=29/23=126%. The latter may reflect the better ability of the biosensor serodiagnostic test to detect TB in HIV+ patients. The accuracy and specificity here are probably better than calculated, but appear low because they are measured against the standard of non-blood based diagnostic procedures for tuberculosis that is known to be inaccurate in the HP population (Palmieri et al., 2002). We are of the opinion that our test may be especially accurate in the HP population. It may therefore sensibly replace the current sputum mycobacterial growth test for diagnosing TB in this population.

The improved accuracy of the biosensor assay of approximately 80%, compared to that of the ELISA of 57% (Schleicher et al., 2002) comes about by two mechanisms:

First, the cholesterol cross-reactivity can be eliminated in the biosensor, reducing the number of false positives and second, the washing steps after antibody addition in ELISA is not required in the biosensor assay, making the latter more sensitive for detection of low affinity antibodies, thereby reducing the number of false negatives.

Remaining false negative scores in the biosensor assay may derive from patients who are under strong immunosuppressive treatment or who suffer immunosuppression due to conditions such as diabetes or cancer.

The biosensor was able to detect low affinity antibody binding to mycolic acids, which the conventional methods cannot achieve. The reason for this can be demonstrated with the biosensor, by showing that antibodies bound to the mycolic acids coated surface wash away if a washing step is introduced (data not shown). In an ELISA assay, the washing step is essential before the final development and many patients therefore tested false negative with this standard technology. The success of the biosensor therefore lies in its reliable detection of antibodies of even low affinity to mycolic acids and in its ability to discriminate between binding to related antigens. Any other technology that can meet these requirements may also be used to diagnose tuberculosis infection based on the detection of anti-mycolic acid antibodies as surrogate markers for tuberculosis.

The novel serodiagnostic method presented here appears to be particularly amenable to the diagnosis of tuberculosis infection in an environment where there is a high prevalence of AIDS and HIV Infection. This appeared to be a major stumbling block in published, state of the art approaches to the serodiagnosis of tuberculosis, even when using lipids from the mycobacterial cell wall as antigens (Boggian et al., 1996).

The Applicant believes that no serodiagnostic assay for tuberculosis is currently accepted, despite the progress reported in studies of antibodies to *M. tuberculosis* in the serum of patients with TB using various antigens (Lyashchenko et al., 1998; Pan et al., 1999; Julian et al., 2002; Schleicher et al., 2002; Lopez-Marin et al., 2003; Pottunarthy et al., 2000, Samanich et al., 2000, Moran et al., 2001). Although Antunes et al., (2002) described the MycoDot serological assay for tuberculosis that is based on the detection of specific IgG antibodies against the lipoarabinomannan (LAM) antigen, the sensitivity values observed were definitely lower in cases of TB associated with HIV, which refuted the usefulness of the test in regions where HIV is highly endemic. LAM as an antigen seems to be satisfactory only in the serodiagnosis of TB as long as HIV is not prevalent in the population.

The advantage of the invention is that it provides a highly predictive, simple, accurate and rapid method to detect antibodies to mycolic acids from blood samples as surrogate markers for pathogenic mycobacterial infection in human and animal subjects. This may then be used in:

1. Rapid diagnosis of pulmonary tuberculosis and other diseases caused by pathogenic mycobacterial infection; i.e. within 3 to 8 hours from sampling.
2. Rapid diagnosis of tuberculosis in organs other than the lungs, i.e. diagnosis that cannot be achieved by the analysis of lung sputum samples, such as renal, skin, pleural or spinal tuberculosis.
3. Diagnosis of tuberculosis infection in HIV co-infected patients.
4. Monitoring the compliance of tuberculosis patients with their treatment regime or the induction of drug resistance by rapid detection of remission of disease.
5. Lowering the cost and complexity of diagnosing tuberculosis.

Furthermore, the experimental evidence indicates that antibodies to mycolic acids occur in most (78%) of the blood samples that were obtained from seriously ill, hospitalised individuals that were infected with *M. tuberculosis* and that such antibodies were generally (82%) not found in the blood samples of an equal number of seriously ill, hospitalized individuals that were not infected with *M. tuberculosis*.

The invention also takes into account experimental evidence indicating that cholesterol is a cross-reactive antigen with mycolic acids in antibody binding and that cholesterol is a weaker antigen than mycolic acids for binding with anti-mycolic acid antibodies. Specificity of binding of anti mycolic acid antibodies is therefore demonstrated in the method. Pre-incubation of blood samples with mycolic acids, but not cholesterol at the same molar concentration, inhibits the interaction of anti-mycolic acids antibodies with immobilised mycolic acids. The method therefore measures both the binding of antibodies to the mycolic acids and the inhibition of binding by pre-incubating the blood samples with mycolic acids. The method therefore has the advantage in that the endpoint of the assay is the degree of inhibition of binding of serum immunoglobulin to mycolic acids after pre-incubation of the serum with solubilized mycolic acids. Furthermore, the endpoint of the method can be determined consistently in an evanescent field biosensor (wave guide or surface plasmon resonance) that allows the binding of low affinity antibodies, and their inhibition of binding when the blood sample is pre-incubated with the mycolic acid antigen. It cannot be consistently determined with standard immunoassays, such as ELISA, that are biased towards higher affinity antibodies and cannot distinguish reliably between binding of antibodies to mycolic acid or cholesterol.

REFERENCES

Alving, C. R., Wassef, N. M., 1999. Naturally occurring antibodies to cholesterol: a new theory of LDL cholesterol metabolism. Immunol. Today 20(8), 362-366.

Antunes, A., Nina, J., David, S., 2002. Serological screening for tuberculosis in the community: an evaluation of the Mycodot procedure in an African population with high HIV-2 prevalence (Republic of Guinea-Bissau). Res. Microbiol. 153, 301-305.

Beckman, E. V., Porcelli, S. A., Morita, C. T. Behar, S. M., Furlong, S. T., Brenner, M. B., 1994. Recognition of a lipid antigen by CD1-restricted αβ+ T cells. Nature 372, 691-694.

Boggian, K., Fierz, W., Vernazza, P. L., 1996. Infrequent detection of lipoarabinomannan antibodies in human immunodeficiency virus-associated mycobacterial disease. Swiss HIV Cohort Study. J. Clin. Microbiol. 34:1854-5.

Brennan P. J., Nikaido H., 1995. The envelope of mycobacteria. Annu. Rev. Biochem. 64:29-63.

Butler, W. R., Jost, K. C., Kilburn, J. O., 1991. Identification of mycobacteria by high-performance liquid chromatography. J. Clin. Microbiol. 29:2468-2472.

Buckle, P. E., Davies, R. J., Kinning, T., Yeung, D., Edwards, P. R., Pollard-Knight, D., 1993. The resonant mirror: a novel optical sensor for direct sensing of biomolecular interactions Part II: Applications. Biosens. Bioelectron. 8, 355-363.

Chan, E. D., Reves, R., Belisie, J. T., Brennan, P. J., Hahn, W. E., 2000. Diagnosis of tuberculosis by a visually detectable immunoassay for lipoarabinomannan. Am. J. Respir. Crit. Care Med. 161, 1713-1719.

Charnace, G., Delacourt, C. 2001. Diagnostic techniques in paediatric tuberculosis. Paediatr. Respir. Rev. 2, 120-125.

Cush, R., Cronin, J. M., Stewart, W. J., Maule, C. H., Molloy, J., Goddard, N. J., 1993. The resonant mirror: a novel optical biosensor for direct sensing of biomolecular interactions Part I: Principle of operation and associated instrumentation. Biosens. Bioelectron. 8, 347-353.

Dijkstra, J., Swartz, G. M., Raney, J. J., Aniagolu, J., Toro, L., Nacy, C. A., Green S. J., 1996. Interaction of anti-cholesterol antibodies with human lipoproteins. J. Immunol. 157(5), 2006-2013.

Fenton M. J. and Vermeulen M. V., 1996. Immunopathology of Tuberculosis: Roles of Macrophages and Monocytes. *Minireview Infect. Immun.* 64:683-690.

Foulds, J., O'Brien, R., 1998. New tools for the diagnosis of tuberculosis: The perspective of developing countries. Int, J, Tuberc. Lung Dis. 2(10), 778-783.

Goodrum, M. A., Siko, D. G. R., Niehues, T., Eichelbauer, D., Verschoor, J. A., 2001. Mycolic acids from *Mycobacterium tuberculosis*: purification by countercurrent distribution and T-cell stimulation. Microbios 106, 55-67.

Heym B., Honore N., Truffot-Pernot C., Banerjee A., Schurra C., Jacobs Jr. W. R., Van Embden J. D. A., Grosset J. H. and Cole S. T., 1994. Implications of multidrug resistance for the future of short-course chemotherapy of tuberculosis: a molecular study. *Lancet* 344:293-298.

Horvath, A., Biro, A., 2003. Anti-cholesterol antibodies in human sera. Autoimmunity Rev. 2, 272-277.

Horvath, A., Fust, G., Horvath, I., Vallus, G., Duba, J., Harcos, P., Prohaszka, Z., Rajnavolgyi, E., Janoskuti, L., Kovacs, M., Csaszar, A., Romics, L., Karadi, I., 2001. Anti-cholesterol antibodies (ACHA) in patients with different atherosclerotic vascular disease and healthy individuals. Characterization of human ACHA. Atherosclerosis 156, 185-195.

Johnson, T., 2000. "WHO urges Asia to implement low-cost strategy to halt TB". Kyodo News Service, 23 March.

Julian, E., Matas, L., Perez, A., Alcaide, J., Laneelle, M., Luquin, M., 2002. Serodiagnosis of Tuberculosis: Comparison of Immunoglobulin A (IgA) Response to Sulfolipid I with IgG and IgM Responses to 2,3-Diacyltrehalose, 2,3,6-Triacyltrehalose, and Cord Factor Antigens. J. Clin. Microbiol. 40(10), 3782-3788.

Kivihya-Ndugga, L., van Cleeff, M., Juma, E., Kimwomi, J., Githui, W., Oskam, L., Schuitema, A., van Soolingen, D., Nganga, L., Kibuga, D., Odhiambo, J., Klatser, P., 2004. Comparison of PCR with the routine procedure for diagnosis of tuberculosis in a population with high prevalences of tuberculosis and human immunodeficiency virus. J. Clin. Microbiol. 42:1012-5.

Lawn S. D., Butera S. T., and Shinnick T. M., 2002. Tuberculosis unleashed: the impact of human immunodeficiency virus infection on the host granulomatous response to *Mycobacterium tuberculosis*. Microbes Infect. 4: 635-646.

Kaufmann S. H. E. and Hess J., 2000. Immune response against *Mycobacterium tuberculosis*: Implications for vaccine development. *J. Biotech.* 83:13-17.

Lee, R. E., Brennan, P. J., Besra G. S., 1996, *Mycobacterium tuberculosis* cell envelope. Curr. Top. Microbiol. Immunol. 215:1-27.

Lopez-Marin, L. M., Segura, E., Hermida-Escobedo, C., Lemassu, A., Salinas-Carmona, M. C., 2003. 6,6'-Dimycoloyl trehalose from a rapidly growing *Mycobacterium*: an alternative antigen for tuberculosis serodiagnosis. FEMS. Immunol. Med. Microbiol. 36: 47-54.

Lyashchenko, K. P., Colangeli, R., Houde, M., Jahdali, H., Menzies, D., Gennaro, M. L., 1998. Heterogeneous antibody responses in tuberculosis. Infect. Immun. 66(8), 3936-3940.

Moody, D. B., Reinhold, B. B., Guy, M. R., Beckman, E. M., Frederique, D. E., Furlong, S. T., Ye, S., Reinhold, V. N., Sieling, P. A., Modlin, R. L., Besra, G. S., Porcelli, S. A., 1997. Structural requirements for glycolipid antigen recognition by CD1b-restricted T cells. Science 278(5336), 283-286.

Moody, D. B., Reinhold, B. B., Reinhold, V. N., Besra, G. S., Porcelli S. A., 1999. Uptake and processing of glycosylated mycolates for presentation to CDb-restricted T cells. Immunol. Lett. 65, 85-91.

Moran. A. J., Treit. J. D., Whitney. J. L., Abomoelak. B., Houghton. R., Skeiky. Y. A. W., Sampaio. D. P., Badaro. R., Nano, F. E., 2001. Assessment of the serodiagnostic potential of nine novel proteins from *Mycobacterium tuberculosis*. FEMS. Microbiol. Lett. 198, 31-36.

Myszka, D. G., 1999. Survey of the 1998 optical biosensor literature. J. Mol. Recognit. 12, 390-408.

Narain J. P., Raviglione M. A. and Kochi A., 1992. HIV-associated tuberculosis in developing countries: epidemiology and strategies for prevention. *Tuberc. Lung Dis.* 73:311-321.

O'Brien, R., 1995. The challenge of tuberculosis: statements on global control and prevention. Prevention in developing countries. (Lancet Conference). *Lancet* 346: 814-816.

Palmieri, F., Girardi, E., Pellicelli, A. M., Rianda, A., Bordi, E., Rizzi, E. B., Petrosillo, N., Ippolito, G., 2002. Pulmonary tuberculosis in HIV infected patients presenting with normal chest radiograph and negative sputum smear. Infection 30:68-74.

Pan, J., Fujiwara, N., Oka, S., Maekura, R., Ogura, T., Yano, I., 1999. Anti-Cord Factor (Trehalose 6,6'-Dimycolate) IgG antibody in tuberculosis patients recognizes mycolic acid subclasses. Microbiol. Immunol. 43(9), 863-869.

Porcelli, S. A., Morita, C. T., Modlin, R. L., 1996. T-cell recognition of non-peptide antigens. Curr. Opin. Immunol. 8, 510-516.

Pottunarthy, S., Wells, V. C., Morris, A. J., 2000. A Comparison of seven tests for serological diagnosis of tuberculosis. J. Clin. Microbiol. 38(6), 2227-2231.

Raqib R., Rahman J., Kamaluddin A. K. M., Kamel S. M. M., Banu F. A., Ahmed S., Rahim Z., Bardhan P. K. Anderson J., and Sack D. A., 2003. Rapid diagnosis of active tuberculosis by detecting antibodies from lymphocyte secretions. *J infect Dis.* 188: 364-370.

Reischl, U., 1996. Application of molecular biology-based methods to the diagnosis of Infectious diseases. Front. Biosci. 1, 72-77.

Samanich, K. M., Keen, M. A., Vissa, V. D., Harder, J. D., Spencer, J. S., Belisle, J. T., Zolla-Pazner, S., Laal, S., 2000. Serodiagnostic potential of culture filtrate antigens of *Mycobacterium tuberculosis*. Clin. Diagn. Lab. Immunol. 7(4), 662-668.

Schleicher, G. K., Feldman, C., Vermaak, Y., Verschoor, J. A., 2002. Prevalence of anti-mycolic acid antibodies in patients with pulmonary tuberculosis co-infected with HIV. Clin. Chem. Lab. Med. 40(9), 882-887.

Siko, D. G. R., 2002. Mycobacterial mycolic acids as immunoregulatory lipid antigens in the resistance to tuberculosis. Ph.D. Thesis, Department of Biochemistry, Faculty of Biological and Agricultural Sciences, University of Pretoria.

Verschoor, J. A., Bye, S. N., 1995. A method for detecting the presence of a *mycobacterium* species and a kit and antibodies for use therein. Patent application no. PCT/GB95/00856.

Verschoor, J. A., 1996. The isolation and purification of mycobacterial lipid cell-wall components. Patent application no. PCT/GB96/00416.

Verschoor, J. A., Lenaerts, A. & Johannsen, E., 1998. A composition comprising a carrier and a purified mycobacterial lipid cell-wall component and its use in the prevention, treatment and diagnosis of disease. Patent application no. PCT/GB98/00681.

Voelker, R., 1995. New initiative for global TB control. The Journal of the American Medical Association 274:1255-1257.

WHO, 1993. WHO attacks global neglect of tuberculosis crisis. Millions dying from 'low priority' disease. [Press release].

The invention claimed is:

1. A method of diagnosing tuberculosis by detecting a surrogate marker for active tuberculosis, the method including the steps of taking up isolated mycolic acid antigen of tuberculous mycobacterial origin or a synthetic analogue thereof in a liposome carrier to produce mycolic acid antigen-containing liposomes;

immobilizing isolated mycolic acid antigen of tuberculous mycobacterial origin to produce immobilized antigens of tuberculous mycobacterial origin;

obtaining a sample from a human or animal suspected of having active tuberculosis, which sample may contain surrogate marker antibodies to the immobilized antigen, dividing the sample into a first, a second and a third sample, the first sample having a lower concentration by dilution than the second and third samples;

exposing part of the first sample to the immobilized mycolic acid antigen in a test vessel;

exposing part of the first sample to the immobilized mycolic acid antigen in a control vessel;

exposing the second sample to mycolic acid antigen-containing liposomes;

exposing the third sample to liposomes not containing the mycolic acid antigen;

adding the second sample, after exposure to the mycolic acid antigen-containing liposomes, to the test vessel;

adding the third sample, after exposure to the liposomes not containing the mycolic acid antigen, to the control vessel;

detecting binding of antibodies to the immobilized mycolic acid antigen in both the test and control vessels in real time; and comparing the degree or extent of binding between the test and the control vessels, any observed lesser binding in the test vessel being an indicator of the presence of antibodies to the mycolic acid antigen in the sample that indicates active tuberculosis in the human or animal from which the sample originated.

2. A method as claimed in claim 1, in which the mycobacterial infection is of the type which causes diseases selected from pulmonary and extra- pulmonary tuberculosis.

3. A method as claimed in claim 1, in which the mycolic acid antigen is extracted from Mycobacterium tuberculosis.

4. A method as claimed in claim 1, in which the mycolic acid antigen is in a form selected from homogenous and heterogenous compound mixtures.

5. A method as claimed in claim 1, in which the mycolic acid antigen-containing liposomes are immobilized on an activated surface.

6. A method as claimed in claim 5, in which the activated surface is a hydrophilic, underivatized biosensor cuvette surface which has been activated by prior incubation with a surface binding agent linked to a hydrophobic hydrocarbon.

7. A method as claimed in claim 1, in which the sample of human or animal origin is selected from blood samples, spinal fluid samples and samples that naturally contain antibodies.

8. A method as claimed in claim 1, in which the sample is from an HIV positive human.

9. A method as claimed in claim 1, in which the antibodies are antibodies against Mycobacterium tuberculosis, or antibodies against mycolic acid components thereof.

10. A method as claimed in claim 9, in which the antibodies are of the type that demonstrate cross-reactivity towards sterols.

11. A method as claimed in claim 10, in which the antibodies are low affinity antibodies.

12. A method as claimed in claim 1, in which exposure of the second sample of human or animal origin to mycolic acid antigen includes pre-incubation of the second sample with liposomes containing mycolic acid antigen.

13. A method as claimed in claim 1, which includes pre-incubation of the third sample with empty liposomes, or liposomes containing phospholipid only.

14. A method as claimed in claim 1, in which exposure of the first sample of human or animal origin to mycolic acid antigen in the test and control vessels includes exposing the samples of human or animal origin to a surface prepared by the prior coating of the surface with mycolic acid antigen and a blocking reagent which prevents non-specific binding of antibodies.

15. A method as claimed in claim 1, which is carried out in a biosensor selected from resonant mirror biosensors, surface plasmon resonance biosensors or piezo-electrical biosensors.

* * * * *